US012036322B2

(12) United States Patent
Craig et al.

(10) Patent No.: US 12,036,322 B2
(45) Date of Patent: *Jul. 16, 2024

(54) GELLING MULTIPARTICULATES

(71) Applicant: Capsugel Belgium NV, Bornem (BE)

(72) Inventors: Christopher D. Craig, Bend, OR (US); Cody Prather, Bend, OR (US)

(73) Assignee: Capsugel Belgium NV, Bornem (BE)

( * ) Notice: Subject to any disclaimer, the term of this patent is extended or adjusted under 35 U.S.C. 154(b) by 0 days.

This patent is subject to a terminal disclaimer.

(21) Appl. No.: 17/977,902

(22) Filed: Oct. 31, 2022

(65) Prior Publication Data

US 2023/0063064 A1 Mar. 2, 2023

Related U.S. Application Data

(63) Continuation of application No. 16/755,130, filed as application No. PCT/EP2018/077523 on Oct. 9, 2018, now Pat. No. 11,510,877.

(60) Provisional application No. 62/570,406, filed on Oct. 10, 2017.

(51) Int. Cl.
*A61K 9/16* (2006.01)
*A61K 9/14* (2006.01)
*A61K 31/522* (2006.01)

(52) U.S. Cl.
CPC .......... *A61K 9/1635* (2013.01); *A61K 9/1611* (2013.01); *A61K 9/1652* (2013.01); *A61K 9/1682* (2013.01); *A61K 31/522* (2013.01); *A61K 9/146* (2013.01)

(58) Field of Classification Search
CPC .. A61K 9/1635; A61K 9/1611; A61K 9/1652; A61K 9/1682; A61K 31/522; A61K 9/146; A61K 31/4166
See application file for complete search history.

(56) References Cited

U.S. PATENT DOCUMENTS

| | | | |
|---|---|---|---|
| 5,087,454 A | 2/1992 | Duerholz et al. | |
| 5,516,543 A | 5/1996 | Amankonah et al. | |
| 5,738,897 A | 4/1998 | Gidley et al. | |
| 5,804,212 A | 9/1998 | Illum | |
| 6,136,363 A | 10/2000 | Bialek et al. | |
| 6,485,771 B1 | 11/2002 | Somerville et al. | |
| 6,607,775 B2 | 8/2003 | Aldred et al. | |
| 7,169,427 B2 | 1/2007 | Frith et al. | |
| 7,494,669 B2 | 2/2009 | Ni et al. | |
| 7,713,551 B2 | 5/2010 | McGurk et al. | |
| 8,236,332 B2 | 8/2012 | Hedges | |
| 8,287,897 B2 | 10/2012 | Fukui | |
| 8,389,012 B2 | 3/2013 | Palaniappan | |
| 9,364,431 B2 | 6/2016 | Callahan | |
| 9,381,160 B2 | 7/2016 | Niichel | |
| 9,579,291 B2 | 2/2017 | Schwarzentruber et al. | |
| 9,603,384 B2 | 3/2017 | Kaliappan et al. | |
| 9,750,275 B2 | 9/2017 | Hayakawa et al. | |
| 11,510,877 B2 * | 11/2022 | Craig | A61K 9/1635 |
| 2002/0012701 A1 | 1/2002 | Kolter et al. | |
| 2003/0045580 A1 | 3/2003 | Einig | |
| 2003/0068407 A1 | 4/2003 | Chiavazza et al. | |
| 2003/0143195 A1 | 7/2003 | Pinsker | |
| 2008/0008814 A1 | 1/2008 | Jackson et al. | |
| 2009/0234022 A1 | 9/2009 | Salentine et al. | |
| 2010/0068276 A1 | 3/2010 | Friesen et al. | |
| 2010/0112139 A1 | 5/2010 | Aumaitre et al. | |
| 2011/0117622 A1 * | 5/2011 | Yoshikado | A61K 9/4891 435/180 |
| 2012/0107468 A1 | 5/2012 | Doyle et al. | |
| 2013/0309363 A1 | 11/2013 | Davidson et al. | |
| 2014/0121191 A1 | 5/2014 | Davidson et al. | |
| 2014/0255583 A1 | 9/2014 | Sarama et al. | |
| 2015/0037269 A1 | 2/2015 | Dumitrescu et al. | |
| 2015/0152301 A1 | 6/2015 | Brandstadt et al. | |
| 2015/0152302 A1 * | 6/2015 | Lam | B29C 73/163 524/29 |
| 2015/0182628 A1 | 7/2015 | Wright et al. | |
| 2015/0252313 A1 | 9/2015 | Fernandez Prieto et al. | |
| 2016/0038569 A1 | 2/2016 | Brakenhielm et al. | |
| 2016/0128943 A1 | 5/2016 | Vepuri et al. | |
| 2016/0165933 A1 | 6/2016 | Lawson et al. | |
| 2016/0235628 A1 | 8/2016 | Zelikman et al. | |
| 2016/0287521 A1 | 10/2016 | Gonzalez et al. | |
| 2017/0000799 A1 | 1/2017 | Tyebji et al. | |
| 2017/0281609 A1 | 10/2017 | Mujumdar | |
| 2017/0290768 A1 | 10/2017 | Barzilay et al. | |
| 2018/0078423 A1 | 3/2018 | Magin et al. | |
| 2018/0169029 A1 | 6/2018 | Aslan et al. | |

(Continued)

FOREIGN PATENT DOCUMENTS

| | | |
|---|---|---|
| EP | 3 078 366 A1 | 10/2016 |
| GB | 2434295 B | 7/2011 |
| GB | 2539744 A | 12/2016 |

(Continued)

OTHER PUBLICATIONS

Cekic et al. ("Preparation and Characterization of Phenytoin-Loaded Alginate and Alginate-Chitosan Microparticles" in Drug Delivery, 14:483-490, 2007) (Year: 2007).*
Liparoti et al., "Supercritical Assisted Atomization: Polyvinylpyrrolidone as Carrier for Drugs with poor Solubility in water" in Journal Of Chemistry, vol. 2013, pp. 1-5). (Year: 2013).*
2004 article on the coloration of tablets and capsule in Manufacturing Chemist. (Year: 2004).*
Propofol, Side Effects, Uses Apr. 2015, (Year: 2015).*
Albertini et al., "New Spray Congealing Atomizer for the Microencapsulation of Highly Concentrated Solid and Liquid Substances," *European Journal of Pharmaceutics and Biopharmaceutics*, vol. 69, No. 1, Oct. 24, 2007, pp. 348-357.

(Continued)

Primary Examiner — Blessing M Fubara
(74) Attorney, Agent, or Firm — Klarquist Sparkman, LLP

(57) ABSTRACT

Multiparticulate compositions including an active agent and a gelling agent are disclosed. The multiparticulate compositions are prepared by an aqueous-based spray and congeal process.

18 Claims, 6 Drawing Sheets

(56) References Cited

U.S. PATENT DOCUMENTS

2020/0323779 A1    10/2020    Craig et al.

FOREIGN PATENT DOCUMENTS

| JP | S57026615 | A | | 2/1982 | | |
|---|---|---|---|---|---|---|
| WO | WO 99/25321 | A1 | | 5/1999 | | |
| WO | WO 01/51031 | A2 | | 7/2001 | | |
| WO | WO 2005/000265 | A2 | | 1/2005 | | |
| WO | WO 2005/053653 | A1 | | 6/2005 | | |
| WO | WO 2006/013084 | A1 | | 2/2006 | | |
| WO | WO-2006013084 | A1 | * | 2/2006 | ........... | A61K 31/415 |
| WO | WO 2012/022498 | A1 | | 2/2012 | | |
| WO | WO 2014/102745 | A1 | | 3/2014 | | |
| WO | WO 2015/097090 | A1 | | 7/2015 | | |
| WO | WO 2016/046817 | A1 | | 3/2016 | | |

OTHER PUBLICATIONS

Belščak-Cvitanović et al., "Improving the Controlled Delivery Formulations of Caffeine in Alginate Hydrogel Beads Combined With Pectin, Carrageenan, Chitosan and Psyllium," *Food Chemistry*, vol. 167, Jul. 11, 2014, pp. 378-386.

Cekić, et al., "Influence of the Preparation Procedure and Chitosan Type on Physicochemical Properties and Release Behavior of Alginate-Chitosan Microparticles," *Drug Development and Industrial Pharmacy*, vol. 35, No. 9, May 19, 2009, pp. 1092-1102.

Cekić, et al., "Preparation and Characterisation of Phenytoin-Loaded Alginate and Alginate-Chitosan Microparticles," *Drug Delivery*, vol. 14, No. 8, Oct. 10, 2008, pp. 483-490.

English translation of CN 114317140 A, Zhao et al., Apr. 12, 2022, 9 pages.

Gaikwad et al., "Enhancement in in Vitro Anti-Angiogenesis Activity and Cytotoxicity in Lung Cancer Cell by Pectin-PVP Based Curcumin Particulates," *International Journal of Biological Macromolecules*, vol. 104, Jun. 9, 2017, pp. 656-664.

International Search Report dated Jan. 25, 2019, issued by the European Patent Office in corresponding International Application No. PCT/EP2018/077523, filed Oct. 9, 2018; 7 pages.

Nayak et al., "Optimization of Aceclofenac-Loaded Pectinate-Poly(Vinyl Pyrrolidone) Beads by Response Surface Methodology," *International Journal of Biological Macromolecules*, vol. 62, Aug. 30, 2013, pp. 194-202.

Nikhar et al., "Gelling Behavior of Different Grades of Chitosan: Comparative Study," *The Pharma Innovation Journal* 2020, 9(3), pp. 431-435.

Nilsen-Nygaard et al., "Chitosan: Gels and Interfacial Properties," *Polymers* 2015, 7, pp. 552-579.

Smith, "The colouration of tablets and capsules," https://manufacturingchemist.com, Jun. 1, 2004, 7 pages.

Written Opinion dated Jan. 25, 2019, issued by the European Patent Office in corresponding International Application No. PCT/EP2018/077523, filed Oct. 9, 2018; 8 pages.

Abbasi et al., "Modeling of Caffeine Release from Crosslinked Water-Swellable Gelatin and Gelatin-Maltodextrin Hydrogels," *Drug Delivery*, Jul. 4, 2008, vol. 15, pp. 455-463.

Bacchi et al., "Turning Liquid Propofol into Solid (without Freezing It): Thermodynamic Characterization of Pharmaceutical Cocrystals Built with a Liquid Drug," *Cryst. Growth Des.*, Sep. 16, 2016, vol. 16, No. 11, pp. 6547-6555, Abstract only, 2 pages.

Chern et al., "Absorption Isotherm of Caffeine and Release Kinetics from Swollen NIPAAm Hydrogels: Experiments and Modeling," *Ind. Eng. Chem. Res.*, Jul. 19, 2004, vol. 43, No. 19, pp. 6150-6156.

Eaimtrakarn et al., "Evaluation of Gastrointestinal Transit Characteristics of Oral Patch Preparation Using Caffeine as a Model Drug in Human Volunteers," *Drug Metabol. Pharmacokin.*, Aug. 6, 2002, vol. 17, No. 4, pp. 284-291.

Muraoka et al., "Evaluation of intestinal pressure-controlled colon delivery capsule containing caffeine as a model drug in human volunteers," *Journal of Controlled Release*, Mar. 2, 1998, vol. 52, Nos. 1-2, pp. 119-129.

Nicoli et al., "Release and Permeation Kinetics of Caffeine From Bioadhesive Transdermal Films," *The AAPS Journal*, Sep. 2, 2005, vol. 7, No. 1, 6 pages.

Sumathi et al., "Release behaviour of drugs from Tamarind Seed Polysaccharide tablets," *J. Pharm Pharmaceut Sci*, Mar. 7, 2002, vol. 5, No. 1, pp. 12-18.

\* cited by examiner

GELLING MULTIPARTICULATES

CROSS-REFERENCE TO RELATED APPLICATIONS

This application is a continuation of U.S. patent application Ser. No. 16/755,130, filed on Apr. 9, 2020, now U.S. Pat. No. 11,510,877, which is the U.S. National Stage of International Application No. PCT/EP2018/077523, filed on Oct. 9, 2018, which was published in English under PCT Article 21(2), which in turn claims the benefit of U.S. Provisional Application No. 62/570,406, filed Oct. 10, 2017, the disclosures of which are incorporated by reference herein in their entireties.

FIELD

This disclosure concerns multiparticulate compositions including an active agent and a gelling agent. The multiparticulate compositions are prepared by an aqueous-based spray and congeal process.

SUMMARY

Embodiments of gelling multiparticulate compositions and methods of making the compositions are disclosed. In some embodiments, a multiparticulate composition comprises a plurality of particles comprising >60 wt % of an active agent, 1-6 wt % of a gelling agent, and up to 39 wt % of a water-soluble polymer. In some embodiments, the water-soluble polymer is not a gelling agent. In certain embodiments, the active agent comprises caffeine. In any or all of the foregoing embodiments, the multiparticulate composition may further comprise a colorant. In any or all of the foregoing embodiments, the plurality of particles may have an average diameter within a range of from 100 μm to 2 mm as measured by laser diffraction.

In any or all of the above embodiments, the gelling agent may comprise gellan gum, carrageenan, agar, pectin, or any combination thereof. In any or all of the above embodiments, the multiparticulate composition may further comprise 0.05-1 wt % of an inorganic salt. In some embodiments, the inorganic salt comprises an alkali metal salt, an alkaline earth metal salt, or a combination thereof. In one embodiment, the gelling agent comprises gellan gum and the inorganic salt comprises calcium chloride. In an independent embodiment, the gelling agent comprises carrageenan and the inorganic salt comprises potassium chloride.

In any or all of the above embodiments, the water-soluble polymer may comprise polyvinylpyrrolidone (PVP), a copolymer of vinylpyrrolidone and vinyl acetate (PVP-VA), polyethylene glycol (PEG), polyethylene oxide (PEO), or any combination thereof. In some embodiments, the water-soluble polymer comprises PVP, such as PVP having a weight average molecular weight of from 30,000 to 50,000 daltons.

In some embodiments, the multiparticulate composition is included in a dosage form such as a capsule, a tablet, or a powder mix.

In some embodiments, a multiparticulate composition as disclosed herein is made by a method including preparing an aqueous suspension comprising an active agent, a gelling agent, and a water-soluble polymer, wherein (i) a concentration of the active agent in the aqueous suspension exceeds a solubility limit of the active agent in the aqueous suspension such that the active agent is not completely dissolved in the aqueous suspension, and (ii) a combined mass of the active agent, the gelling agent, and the water-soluble polymer includes >60 wt % of the active agent, 1-6 wt % of the gelling agent, and up to 39 wt % of the water-soluble polymer; forming droplets of the aqueous suspension, wherein the droplets are formed at a temperature above a gelation temperature of the aqueous suspension; forming congealed particles from the droplets, the congealed particles comprising the active agent, the gelling agent, the water-soluble polymer, and water; and drying the congealed particles to form a plurality of dried particles comprising >60 wt % of the active agent, 1-6 wt % of the gelling agent, and up to 39 wt % of the water-soluble polymer. In some embodiments, the active agent, prior to preparation of the aqueous suspension, has an average particle size within a range of from 20-200 μm. In any or all of the above embodiments, the aqueous suspension may further comprise an inorganic salt, wherein a combined mass of the active agent, the gelling agent, the inorganic salt, and the water-soluble polymer includes >60 wt % of the active agent, 1-6 wt % of the gelling agent, 0.05-1 wt % of the inorganic salt, and up to 38.95 wt % of the water-soluble polymer.

In any or all of the above embodiments, forming droplets of the aqueous suspension may include dispensing the aqueous suspension onto a spinning disk of a rotary atomizer, whereby the aqueous suspension is atomized into droplets. In any or all of the above embodiments, forming the congealed particles from the droplets may include cooling the droplets of the aqueous suspension to a temperature below the gelation temperature of the aqueous suspension. In some embodiments, cooling the droplets of the aqueous composition comprises convective cooling.

In any or all of the above embodiments, preparing the aqueous suspension may further include combining a first portion of the active agent with water preheated to a temperature above the gelation temperature of the aqueous suspension and mixing to form an aqueous solution; adding the gelling agent and the water-soluble polymer to the aqueous solution and mixing to dissolve the gelling agent and the water-soluble polymer while maintaining the aqueous solution at a temperature above the gelation temperature; optionally adding an inorganic salt to the aqueous solution and mixing the aqueous solution while maintaining the aqueous solution at a temperature above the gelation temperature; adding a second portion of the active agent to the aqueous solution to form the aqueous suspension; and maintaining a temperature of the aqueous suspension above the gelation temperature until forming the droplets of the aqueous suspension. In some embodiments, the gelling agent and water-soluble polymer are blended to form a blend, and the blend is added to the aqueous solution. In any or all of the above embodiments, the inorganic salt may be dissolved in water to form an inorganic salt solution, which is then added to the aqueous solution.

In any or all of the above embodiments, (i) the active agent may comprise caffeine, (ii) the water-soluble polymer may comprise PVP, or (iii) both (i) and (ii). In any or all of the above embodiments, the gelling agent may comprise gellan gum and the inorganic salt may comprise calcium chloride, or the gelling agent may comprise carrageenan and the inorganic salt may comprise potassium chloride.

The foregoing and other objects, features, and advantages of the invention will become more apparent from the following detailed description, which proceeds with reference to the accompanying figures.

DETAILED DESCRIPTION

Figure 1:
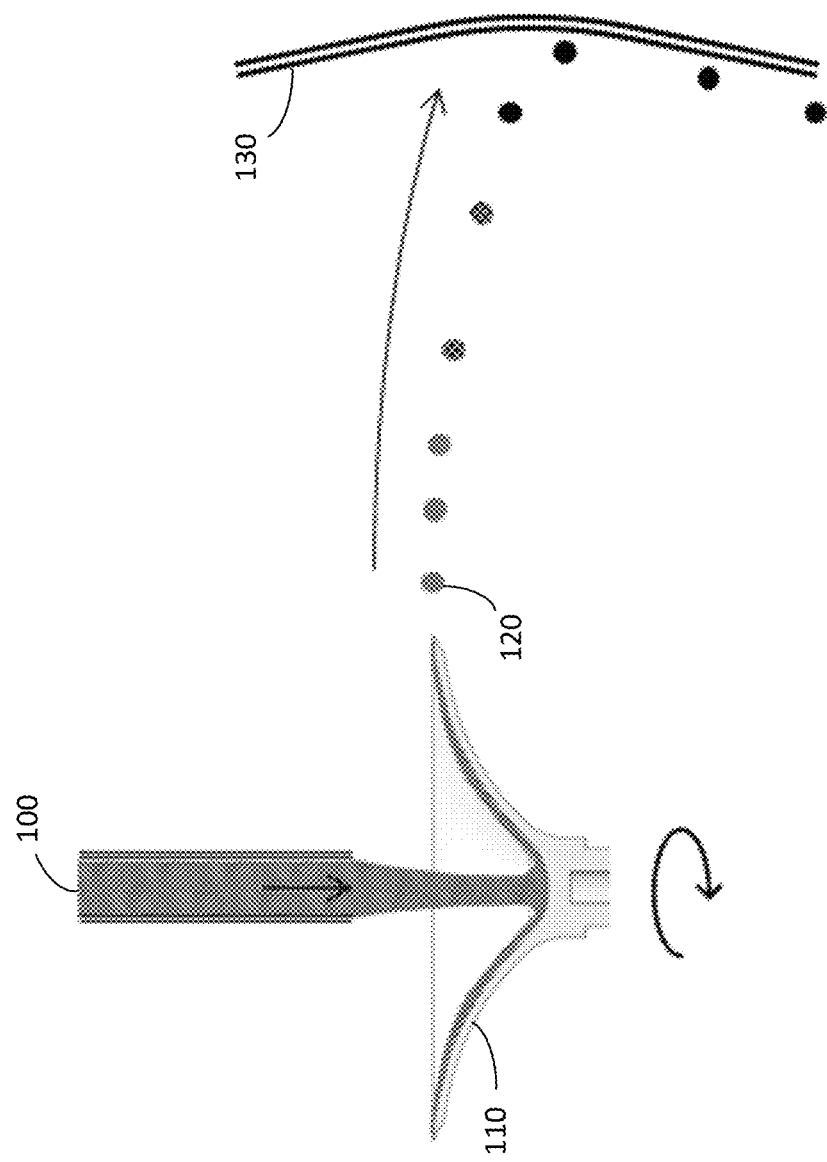
FIG. 1 is a schematic diagram illustrating one embodiment of a method for forming congealed particles by rotary atomization of an aqueous suspension and convective cooling.

Embodiments of multiparticulate compositions including an active agent and a gelling agent are disclosed. The multiparticulate compositions are prepared by an aqueous-based spray and congeal process. The aqueous-based process advantageously allows preparation of multiparticulate compositions including a much higher loading of active agent compared to multiparticulate compositions formed by a conventional melt-spray-congeal process in which a suspension of active agent and molten lipid is atomized and convectively cooled until the lipid solidifies. Multiparticulate compositions produced by melt-spray-congeal processes typically include a maximum of 30-60 wt % of the active agent. In contrast, some embodiments of the disclosed multiparticulate compositions include greater than 60 wt % active agent, such as up to 95 wt % active agent.

I. DEFINITIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Although there are alternatives for various components, parameters, operating conditions, etc. set forth herein, that does not mean that those alternatives are necessarily equivalent and/or perform equally well. Nor does it mean that the alternatives are listed in a preferred order unless stated otherwise.

Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2).

In order to facilitate review of the various embodiments of the disclosure, the following explanations of specific terms are provided:

Active agent: A drug, medicament, pharmaceutical, therapeutic agent, nutraceutical, or other compound that may be administered to a subject to effect a change, such as treatment, amelioration, or prevention of a disease, disorder, or condition, or at least one symptom associated therewith, or to effect a change in a subject's overall health or wellbeing.

Congealed: Solidified. Congeal generally means to solidify via cooling.

Convective cooling: Cooling by heat transfer due movement of molecules within a fluid, such as a gas. As used herein, convective cooling refers to cooling of atomized droplets traveling through a gas, e.g., in a cooling chamber.

Copolymer: A polymer formed from polymerization of two or more different monomers.

Dispersity: A measure of the heterogeneity of particle sizes in a population of particles. Particles are considered to be monodisperse if the particles have roughly the same size, shape, and/or mass. Particles are considered to be polydisperse if the size, shape, and/or mass distribution is variable.

Free water: As used herein, the term "free water" refers to unbound water, i.e., water that can be removed from solid particles by evaporation or drying at a temperature <100° C. Free water includes surface water and water that is not trapped within a crystal structure or adsorbed/bound (e.g., by hydrogen bonding) to components within the particles.

Gel: A colloidal system comprising a solid three-dimensional network within a liquid. By weight, a gel is primarily liquid, but behaves like a solid due to a three-dimensional network of entangled and/or crosslinked molecules of a solid within the liquid. From a rheological perspective, a gel has a storage modulus G' value which exceeds that of the loss modulus G". The storage modulus is a measure of the energy stored in a material in which a deformation (e.g., sinusoidal oscillatory shear) has been imposed; storage modulus can be thought of as the proportion of total rigidity of a material that is attributable to elastic deformation. The loss modulus is a measure of the energy dissipated in a material in which a deformation (e.g., sinusoidal oscillatory shear) has been imposed; loss modulus can be thought of as the proportion of the total rigidity of a material that is attributable to viscous flow rather than elastic deformation. The storage modulus and loss modulus can be determined with a rheometer.

Gelation temperature: The temperature threshold for the formation of a gel. From a rheological perspective, the gelation temperature is the temperature at which tan delta, the ratio of the loss modulus G" to the storage modulus G' becomes equal to 1, i.e., when G"=G'. When tan delta is less than 1, the composition exhibits solid-like behavior, i.e., a gel. When tan delta is greater than 1, liquid-like behavior predominates. The storage modulus and loss modulus can be determined with a rheometer.

Gelling agent: A substance that stabilizes and/or thickens a liquid or sol (colloidal suspension) to provide a gel. A thermogelling agent is a substance that forms a three-dimensional network within a liquid when subjected to a temperature change. Some thermogelling agents form a gel when heated above a certain temperature; other thermogelling agents form a gel when the temperature is decreased below a certain threshold.

Gelling aid: A substance (e.g., a compound or ion) that facilitates, or is required for, gelation of a gelling agent. For example, certain cations facilitate gelation of gellan gum.

Multiparticulate composition: A composition comprising a plurality of discrete particles.

Polymer: A molecule of repeating structural units (e.g., monomers) formed via a chemical reaction, i.e., polymerization.

Solution: A homogeneous mixture composed of two or more substances. A solute (minor component) is dissolved in a solvent (major component). A plurality of solutes and/or a plurality of solvents may be present in the solution.

Span: A measure of dispersity. When particle sizes are measured by laser diffraction, span is defined as $$\text{Span} = \frac{D_{v0.9} - D_{v0.1}}{D_{v0.5}}$$

where D is the particle distribution, 90% of the particle distribution lies below $D_{v0.9}$ (i.e., 90% of the particles are smaller than the size indicated as $D_{v0.9}$) and 10% of the particle distribution lies below $D_{v0.1}$.

Spheroid: Sphere-like, but not perfectly spherical. A spheroid is a quadric surface obtained by rotating an ellipse about one of its principal axes.

Surface mean diameter D[3,2]: The surface mean diameter determined by laser diffraction is defined as $$D[3, 2] = \frac{\sum_i^n D_i^3 v_i}{\sum_1^n D_i^2 v_i}$$

where n is the number of channels and $D_i v_i$ is the geometric mean of the particle diameters within a given channel.

Suspension: A heterogeneous mixture in which particles are dispersed substantially uniformly in a liquid or gaseous medium. A liquid suspension in which the dispersed particles have a diameter between about 1-100 nm is considered to be a colloidal suspension. The particles in a colloidal suspension tend to remain in suspension. If the particles have a diameter larger than about 100 nm, they typically will settle if undisturbed and form a sediment.

Syneresis: Contraction of a gel accompanied by the separating out of liquid from the gel.

Volume mean diameter D[4,3]: The volume mean diameter determined by laser diffraction is defined as $$D[4, 3] = \frac{\sum_i^n D_i^4 v_i}{\sum_1^n D_i^3 v_i}$$

where n is the number of channels and $D_i v_i$ is the geometric mean of the particle diameters within a given channel.

Weight Average Molecular Weight:

$$Mw = \frac{\sum N_i M_i^2}{\sum N_i M_i}$$

where $M_i$ is the molecular weight of a chain, and $N_i$ is the number of chains of that molecular weight. Weight average molecular weight is determined by methods that are sensitive to molecular size, such as light-scattering techniques, small angle neutron scattering, X-ray scattering, and sedimentation velocity.

II. MULTIPARTICULATE COMPOSITIONS

Disclosed herein are embodiments of multiparticulate compositions comprising a plurality of particles. The multiparticlulate composition comprises an active agent, a water-soluble polymer, and a gelling agent present in sufficient concentration to produce a gel in combination with the active agent, water-soluble polymer, and an aqueous solvent under certain temperature conditions. The multiparticulate composition may further comprise an inorganic salt. Some gelling agents require an inorganic salt for gelation and/or exhibit better gelling performance in combination with an inorganic salt. Advantageously, some embodiments of the disclosed multiparticulate compositions include a high loading of the active agent, such as a loading >60 wt %.

In some embodiments, the plurality of particles comprises >60 wt % of an active agent, 1-6 wt % of a gelling agent, and up to 39 wt % of a water-soluble polymer. In certain embodiments, the plurality of particles comprises >60 wt % of an active agent, 1-6 wt % of a gelling agent, 0.05-1 wt % of an inorganic salt, and up to 38.95 wt % of a water-soluble polymer. In some examples, the compositions of individual particles within the plurality of particles are substantially the same, i.e., the compositions of individual particles vary by no more than ±10% relative to an average composition of the plurality of particles. In certain embodiments, at least 90% or at least 95% of the particles individually comprise >60 wt % of the active agent, 1-6 wt % of the gelling agent, and up to 39 wt % of the water-soluble polymer. If an inorganic salt is present, at least 90% or at least 95% of the particles may individually comprise >60 wt % of the active agent, 1-6 wt % of the gelling agent, 0.05-1 wt % of the inorganic salt, and up to 38.95 wt % of the water-soluble polymer. In some embodiments, the water-soluble polymer is not a gelling agent.

Suitable gelling agents include thermogelling or temperature responsive agents, such as thermogelling agents that form a gel when the temperature of the gelling agent, or a composition comprising the gelling agent, is reduced below a certain threshold. Thermogelling agents that gel when cooled include, but are not limited to, certain natural gums (e.g., gellan gum), polysaccharides (e.g., carrageenan (e.g., i (iota) type carrageenan, κ (kappa) type carrageenan, and/or λ (lambda) type carrageenan), agar (or agar-agar), agarose, pectin), and proteins (e.g., gelatin), among others. Gelation may be reversible or irreversible. Advantageously, the gelling agent produces has a moderate-to-high temperature gel point (e.g., 30-80° C.), exhibits little or no syneresis, and/or produces robust particles as discussed further below. In some embodiments, the gelling agent is gellan gum (natural gellan and/or low-acyl gellan), carrageenan, agar, gelatin, pectin, or a combination thereof. In certain embodiments, the gelling agent is gellan gum, carrageenan, or a combination thereof. In some embodiments, the plurality of particles comprises 1-6 wt % gelling agent, such as 1-5 wt %, 1-4 wt %, 1-3 wt %, or 1.5-2.5 wt % gelling agent.

In any or all of the above embodiments, the disclosed multiparticulate compositions may further comprise an inorganic salt. The inorganic salt may be required for and/or may facilitate gelation of the gelling agent. In some embodiments, the inorganic salt increases the gelation temperature of an aqueous suspension comprising the gelling agent. Suitable inorganic salts include, but are not limited to, inorganic salts comprising monovalent or divalent cations, e.g., alkali metal and alkaline earth metal salts. In some embodiments, the inorganic salt comprises an alkali metal halide, an alkaline earth metal halide, or a combination thereof. Exemplary salts include $K^+$, $Na^+$, and $Ca^{2+}$ salts, among others. In certain embodiments, the salt is a chloride salt. In one embodiment, the gelling agent comprises gellan gum and the inorganic salt comprises calcium chloride. In an independent embodiment, the gelling agent comprises carrageenan and the inorganic salt comprises potassium chloride. In some embodiments, the plurality of particles comprises 0.05-1 wt % of an inorganic salt, such as 0.1-1 wt %, 0.1 to 0.8 wt %, or 0.1-0.6 wt %.

Embodiments of the disclosed multiparticulate compositions comprise an active agent. In any or all of the above embodiments, the active agent may be any drug, medicament, pharmaceutical, therapeutic agent, nutraceutical, or other compound that may be administered to a subject to effect a change, such as treatment, amelioration, or prevention of a disease, disorder, or condition, or at least one symptom associated therewith, or to effect a change in a subject's overall health or wellbeing (e.g., such as by reducing fatigue, correcting a mineral or vitamin deficiency, mitigating insomnia, or augmenting a subject's immune system). In one embodiment, the active agent is aqueous soluble with a solubility of at least 1 mg/mL, at least 5 mg/mL, or at least 10 mg/mL in an aqueous solution at 25° C. In certain embodiments, the active agent remains soluble in aqueous solution at temperatures up to 95° C. In an independent embodiment, the active agent is poorly aqueous soluble with a solubility of from 0.05-1 mg/mL in aqueous solution at 25° C. In another independent embodiment, the active agent is not an ionic compound. In still another independent embodiment, the active agent is an ionic compound, such as an anionic salt of a drug, medicament, pharmaceutical, therapeutic agent, or nutraceutical. In another independent embodiment, the active agent is not a cationic salt comprising a monovalent or divalent metal cation. In yet another independent embodiment, the active agent is a thermally-stable active, such as thermally stable in aqueous solution at temperatures up to 95° C. In still another independent embodiment, the active agent in the particles is crystalline or substantially crystalline, such as at least 90 wt % or at least 95 wt % crystalline. It is understood that an active agent may include any of the foregoing properties in combination, unless such properties are mutually exclusive. In any or all of the foregoing embodiments, the identity and/or quantity of the active agent may affect gelation temperature of an aqueous solution or aqueous suspension including the gelling agent and the active agent. Caffeine, for instance, increases gelation temperature of an aqueous suspension including a gelling agent and caffeine. Exemplary active agents include, but are not limited to, stimulants such as caffeine, other small-molecule (e.g., typically having a molecular weight <900 daltons) health and nutritional additives, phenytoin, other small-molecule medicines, and combinations thereof. In certain embodiments, the active agent is caffeine. In an independent embodiment, the active agent is phenytoin. In any or all of the above embodiments, the multiparticulate composition may comprise >60 wt % active agent. In some embodiments, the plurality of particles comprises from greater than 60 wt % to 95 wt % active agent, such as 65-95 wt %, 65-90 wt %, 70-90 wt %, 75-90 wt %, or 80-90 wt % active agent.

In any or all of the above embodiments, the multiparticulate composition may further comprise up to 39 wt % of a water-soluble polymer. In some embodiments, the water-soluble polymer is not a gelling agent. In certain embodiments, the aqueous solubility of the water-soluble polymer increases as temperature increases. Suitable water-soluble polymers include, but are not limited to, polyvinylpyrrolidone (PVP), a copolymer of vinylpyrrolidone and vinyl acetate (PVP-VA, such as PVP-VA64 having a VP/VA w/w ratio of 60/40), polyethylene glycol (PEG), polyethylene oxide (PEO, a polymer of ethylene oxide having a weight average molecular weight of greater than 100,000 daltons), and combinations thereof. In some embodiments, the water-soluble polymer comprises, consists essentially of, or consists of PVP. In any or all of the above embodiments, the multiparticulate composition may comprise 0.1-38.9 wt % of the water-soluble polymer. In some embodiments, the plurality of particles comprises 4-39 wt %, 4-34 wt %, 9-34 wt %, 14-34 wt %, 19-34 wt %, or 24-34 wt % of the water-soluble polymer. In any or all of the above embodiments, the water-soluble polymer may have a weight average molecular weight within a range of 20,000-200,000 daltons, such as within a range of 20,000-150,000 daltons, 20,000-100,000 daltons, 25,000-75,000 daltons or 30,000-50,000 daltons. In certain embodiments, the water-soluble polymer is PVP having a weight average molecular weight within a range of 30,000-50,000 daltons, such as PVP-K30 with a molecular weight ranging from 35,000-51,000 and a weight average molecular weight of 40,000 daltons. In any or all of the foregoing embodiments, inclusion of the water-soluble polymer may increase robustness (i.e., resistance to crushing, resistance to fragmentation, and/or decreased friability) of the particles. In some examples, particles including the water-soluble polymer remained substantially the same size (e.g., a change of 0-4% in diameter) when dispersed at a pressure of 4 bar.

In any or all of the above embodiments, the multiparticulate composition may further comprise a colorant. Suitable colorants include colorants that are safe for use in food, medical, and/or nutraceutical products. Exemplary colorants include, but are not limited to FD&C Blue No. 1 (Brilliant blue FCF), FD&C Blue No. 2 (indigotine), FD&C Green No. 3 (fast green FCF), FD&C Red No. 3 (erythrosine), FD&C Red No. 40 (allura red AC), FD&C Yellow No. 5 (tartrazine), and FD&C Yellow No. 6 (sunset yellow FCF), or a lake pigment of one of the foregoing colorants other than Red No. 3. In some examples, the colorant is a Blue Lake #2. The colorant may be added in any concentration sufficient to provide a desired color intensity in the composition. In some embodiments, the plurality of particles comprises from 0-2 wt % colorant, such as from 0.01-2 wt %, 0.05-2 wt %, 0.1-2 wt %, 0.2-1.5 wt %, or 0.2-1 wt % colorant.

In any or all of the above embodiments, a mass ratio of gelling agent to inorganic salt in the plurality of particles may be within a range of 1-120, such as within a range of 1-100, 1-50, 1-25, 1-20, 1-15, 2-15, or 3-15. Suitable ratios may depend, in part, on particular combinations of gelling agents and inorganic salts. In one embodiment, the gelling agent is gellan gum, the inorganic salt is calcium chloride, and the mass ratio of gellan gum to calcium chloride is within a range of 5-15, such as within a range of 10-15 or 12-15. In an independent embodiment, the gelling agent is carrageenan, the inorganic salt is potassium chloride, and the mass ratio of carrageenan to potassium chloride is within a range of 3-10, such as within a range of 3-7 or 3-5.

In any or all of the above embodiments, a mass ratio of water-soluble polymer to gelling agent in the plurality of particles may be within a range of 0.5-39, such as within a range of 0.5-30, 1-25, 1-15, 5-15, 5-10, 5-8, 5-7.5, or 6-7. Suitable ratios may depend, in part, on particular combinations of water-soluble polymers and gelling agents. In one embodiment, the water-soluble polymer is PVP, the gelling agent is gellan gum, and the mass ratio of PVP to gellan gum is within a range of 5-8, such as within a range of 6.5-7.5. In an independent embodiment, the water-soluble polymer is PVP, the gelling agent is carrageenan, and the mass ratio of PVP to carrageenan is within a range of 5-8, such as within a range of 5.5-6.5.

In any or all of the above embodiments, a mass ratio of water-soluble polymer to inorganic salt in the plurality of particles may be within a range of 4-800, such as within a range of 5-500, 10-250, 20-150, or 20-100. Suitable ratios may depend, in part, on particular combinations of water-soluble polymers and inorganic salts. In one embodiment, the water-soluble polymer is PVP, the inorganic salt is calcium chloride, and the mass ratio of PVP to calcium chloride is within a range of 10-250, such as within a range of 20-150, 20-100, 50-100, or 75-100. In an independent embodiment, the water-soluble polymer is PVP, the inorganic salt is potassium chloride, and the mass ratio of PVP to potassium chloride is within a range of 10-250, 20-150, 20-100, 20-50, 20-40, or 20-30.

Embodiments of the multiparticulate compositions comprise a plurality of particles. In any or all of the above embodiments, the particles may have a spherical, spheroid or substantially spheroid (e.g., having some irregularities in the spheroid) morphology. In any or all of the above embodiments, the plurality of particles may have an average diameter within a range of from 100 µm to 2 mm as measured laser diffraction, e.g., laser diffraction based on Mie theory of light scattering. The diameter may be reported as a surface mean diameter D[3,2] or a volume mean diameter D[4,3]. The surface mean diameter and volume mean diameter may be substantially similar, e.g., D[3,2] may vary from D[4,3] by less than ±10%. Unless indicated otherwise, the average diameter reported herein is D[4,3]. In some embodiments, the plurality of particles has an average diameter within a range of 200 µm to 1.5 mm, 250 µm to 1 mm, 500 µm to 1 mm, or 600 µm to 1 mm. Individual particles may have diameters that fall outside the average diameter range. Advantageously, the particles have a relatively low polydispersity. Polydispersity may be indicated by span. In some embodiments, the plurality of particles has a span within a range of 0.5-0.9, such as a span within a range of 0.6-0.8 or 0.65-0.75.

In any or all of the above embodiments, the particles of the multiparticulate compositions may be robust. By robust is meant that the particle size undergoes little or no change when subjected to pressure titration (i.e., dispersing a plurality of dry particles under pressure and measuring particle size by laser diffraction) over a pressure range of 0.1-4 bar. In some embodiments, the average diameters of the plurality of particles, exhibit little or no change when measured under dispersion pressures ranging from >0.1 bar to 4 bar relative to the average particle diameter measured at a pressure of 0.1 bar, such as an average diameter change of less than ±10%, less than ±5%, less than ±4%, or less than ±3%. In other words, the average particle diameter measured under a dispersion pressure of 4 bar may vary less than ±10%, less than ±5%, less than ±4%, or less than ±3% relative to the average particle diameter measured under a dispersion pressure of 0.1 bar. Thus, in some embodiments the particles are suitable for handling and packaging (e.g., encapsulating) little or no particle fragmentation. Advantageously, some embodiments of the disclosed multiparticulate compositions dissolve more rapidly in aqueous solution, such as in gastric media, than conventional multiparticulate compositions comprising lipids and active agents, wherein the particles are formed by a melt-spray-congeal process.

In some embodiments, the multiparticulate composition comprises, consists essentially of, or consists of >60 wt % of an active agent, 1-6 wt % of a gelling agent, up to 39 wt % of a water-soluble polymer, and 0-2 wt % of a colorant. In certain embodiments, the multiparticulate composition comprises, consists essentially of, or consists of >60 wt % of an active agent, 1-6 wt % of a gelling agent, 0.05-1 wt % of an inorganic salt, up to 38.95 wt % of a water-soluble polymer, and 0-2 wt % of a colorant. As used herein, "consists essentially of" means that the multiparticulate composition does not include any additional components that may materially affect properties of the multiparticulate composition. Thus, the multiparticulate composition does not include components such as non-gelling, water-insoluble polymers, organic salts, plasticizers, lubricants, and the like. However, the multiparticulate composition may include trace amounts (i.e., less than 1 wt %) of components that do not materially affect properties of the multiparticulate composition, such as trace amounts of inert excipients, including inert excipients that may be present in commercially available active agents.

Additionally, the multiparticulate composition may include trace amounts of free water, such as 2 wt % free water.

In one embodiment, the multiparticulate composition comprises, consists essentially of, or consists of (i) 75-95 wt % caffeine, (ii) 1-6 wt % gellan gum, carrageenan, or a combination thereof, (iii) 0.05-0.3 wt % calcium chloride, potassium chloride, or a combination thereof, and (iv) 1-23.95 wt % PVP. In an independent embodiment, the multiparticulate composition comprises, consists essentially of, or consists of (i) 75-95 wt % caffeine, (ii) 1-6 wt % gellan gum, carrageenan, or a combination thereof, (iii) 0.05-0.3 wt % calcium chloride, potassium chloride, or a combination thereof, (iv) 1-23.94 wt % PVP, and (v) 0.01-2 wt % of a colorant. As used herein, "consists essentially of" means that the multiparticulate composition does not include additional active agents, gelling agents, inorganic salts, or polymers besides those recited. However, the multiparticulate composition may include trace amounts of excipients or water as described above. In another independent embodiment, the multiparticulate composition comprises, consists essentially of, or consists of (i) 80-90 wt % caffeine, (ii) 1.5-2.5 wt % gellan gum, carrageenan, or a combination thereof, (iii) 0.1-0.2 wt % calcium chloride, potassium chloride, or a combination thereof, (iv) 6.1-17.6 wt % PVP, and (v) 0.8-1.2 wt % of a colorant. In another independent embodiment, the multiparticulate composition comprises, consists essentially of, or consists of 80-90 wt % caffeine, 1.5-2.5 wt % gellan gum, 0.1-0.2 wt % calcium chloride, 6.1-17.6 wt % PVP, and 0.8-1.2 wt % of a colorant. In still another independent embodiment, the multiparticulate composition comprises, consists essentially of, or consists of 80-90 wt % caffeine, 1.5-2.5 wt % carrageenan, 0.1-0.2 wt % potassium chloride, 6.1-17.6 wt % PVP, and 0.8-1.2 wt % of a colorant. In any or all of the foregoing embodiments, the PVP may be PVP-K30.

In any or all of the above embodiments, the disclosed multiparticulate composition may comprise a plurality of coated particles, wherein the particles disclosed herein further include an outer coating. The outer coating may be any pharmaceutically acceptable coating. In some embodiments, the coating is a polymeric coating, e.g., shellac or a pharmaceutically acceptable salt thereof.

Embodiments of the disclosed multiparticulate compositions may be formulated into dosage forms, such as capsules, tablets, powder mixes, and the like. In some embodiments, the multiparticulate composition is encapsulated to provide a capsule filled with the multiparticulate composition. The capsule shell may be any capsule shell suitable for ingestion, including hard and soft capsule shells. Exemplary capsule shells include, but are not limited to, capsule shells comprising gelatin, hydroxypropyl methylcellulose, and the like. In an independent embodiment, the multiparticulate composition is formulated into a tablet. The tablet may further comprise excipients, e.g., pharmaceutically acceptable binders, glidants, etc. as are known to those of ordinary skill in the art of pharmaceutical formulations. In another independent embodiment, the multiparticulate composition is formulated into a powder mix comprising the multiparticulate composition and a pharmaceutically acceptable bulk agent or matrix material, as are known to those of ordinary skill in the art of pharmaceutical formulations.

III. METHODS OF MAKING MULTIPARTICULATE COMPOSITIONS

Embodiments of the disclosed multiparticulate compositions are formed by an aqueous-based spray and congeal process. Conventional spray and congeal processes are known as melt-spray-congeal (MSC) processes. In a conventional MSC process, an active agent is suspended in a molten lipid and the resulting suspension is sprayed and then convectively cooled to solidify the lipid and provide congealed particles. MSC processes, however, generally are limited to active agent loadings of less than 60 wt %, such as maximum active agent loadings of 30-60 wt %, due to viscosity limitations of the rotary atomization apparatus. Advantageously, embodiments of the disclosed method can be used to produce multiparticulate compositions comprising >60 wt % of an active agent, such as multiparticulate compositions comprising from >60 wt % to 95 wt % of the active agent.

In some embodiments, a method of making the disclosed multiparticulate compositions comprises (i) preparing an aqueous suspension comprising an active agent, a gelling agent, and a water-soluble polymer, (ii) forming droplets of the aqueous suspension, wherein the droplets are formed at a temperature above a gelation temperature of the aqueous suspension, (iii) forming congealed particles from the droplets, the congealed particles comprising the active agent, the gelling agent, the water-soluble polymer, and water, and (iv) drying the congealed particles to form a plurality of dried particles. A combined mass of the active agent, the gelling agent, and the water-soluble polymer includes >60 wt % of the active agent, 1-6 wt % of the gelling agent, and up to 39 wt % of the water-soluble polymer. In some embodiments, the aqueous suspension further comprises an inorganic salt, and the congealed particles comprise the active agent, the gelling agent, the inorganic salt, the water-soluble polymer, and water. In such embodiments, a combined mass of the active agent, the gelling agent, the inorganic salt, and the water-soluble polymer includes >60 wt % of the active agent, 1-6 wt % of the gelling agent, 0.05-1 wt % of the inorganic salt, and up to 38.95 wt % of the water-soluble polymer. In certain embodiments, a concentration of the active agent in the aqueous suspension exceeds a solubility limit of the active agent in the aqueous suspension such that the active agent is not completely dissolved in the aqueous suspension. The aqueous suspension may further include up to 2 wt % of a colorant. In any or all of the foregoing embodiments, the active agent, prior to preparation of the aqueous suspension, may have an average particle size within a range of from 20-200 µm, such as an average particle size of 25-150 µm, 25-100 µm, or 50-100 µm. In some embodiments, the active agent, prior to preparation of the aqueous suspension, is crystalline or substantially (e.g., at least 90 wt %) crystalline. In an independent embodiment, the active agent, prior to preparation of the aqueous suspension, is non-crystalline or substantially (e.g., at least 90 wt %) non-crystalline.

In any or all of the above embodiments, the aqueous suspension may include 30-70 wt % water, such as 40-60 wt % water, or 45-55 wt % water. The amount of water may be selected, in part, based on solubility of the active agent and/or viscosity of the aqueous suspension. Advantageously, the amount of water is selected such that only a portion of the active agent is dissolved in the aqueous suspension. In some embodiments, the amount of water is selected such that the aqueous suspension comprises 15-50 wt % undissolved solids. In certain embodiments, from 50-90 wt % of the active agent is suspended in the aqueous suspension with the remaining active agent being dissolved. The viscosity may be selected to be compatible with the apparatus used to form droplets of the aqueous suspension and/or to provide droplets of a desired size.

Droplets of the aqueous suspension are formed at a temperature greater than a gelation temperature of the aqueous suspension. In some embodiments, the temperature may be within a range of from at least 5° C. greater than the gelation temperature to a temperature <100° C. In some embodiments, the temperature at which the droplets are formed ranges from 5° C. greater than the gelation temperature to 95° C., or from 10° C. greater than the gelation temperature to 95° C. In certain examples, the temperature at which the droplets are formed is within a range of 75-95° C. or 80-90° C. In some embodiments, the aqueous suspension is maintained at a temperature above the gelation temperature of the aqueous suspension prior to forming the droplets. When the active agent is temperature-sensitive (e.g., when prolonged exposure to high temperatures degrades the active agent), the temperature at which the droplets are formed may be near a gelation temperature of the aqueous suspension, e.g., from 5-10° C. greater than the gelation temperature. Additionally, or alternatively, a temperature-sensitive active agent may be added to a heated aqueous suspension or solution comprising the gelling agent, inorganic salt, water-soluble polymer, and optional colorant just prior to forming the droplets such that the aqueous suspension comprising the temperature-sensitive active agent is at a temperature greater than the gelation temperature for less than five minutes, less than two minutes, less than one minute, or less than 30 seconds prior to formation of the droplets. In one embodiment, an aqueous suspension of the temperature-sensitive active agent having a temperature below a temperature at which degradation occurs is added to a heated aqueous suspension or solution comprising the gelling agent, inorganic salt, water-soluble polymer, and optional colorant to form a combined aqueous suspension just prior to forming the droplets, wherein the combined aqueous suspension has a temperature above a gelation temperature of the combined aqueous suspension.

The droplets may be formed by any suitable method including, but not limited to, rotary atomization or spraying through a spray nozzle such as a two-fluid nozzle, a flash nozzle, a pressure nozzle, or a shower head (e.g., a shower head comprising a plurality of atomizing spray nozzles). In some embodiments, forming droplets of the aqueous suspension comprises dispensing the aqueous suspension onto a spinning disk of a rotary atomizer, whereby the aqueous suspension is atomized into droplets. The rotation speed may be selected, based in part, on a desired droplet and subsequent particle size. For example, when producing particles having an average diameter within a range of from 100 μm to 2 mm, the rotation speed may be within a range of 500-8000 rpm, such as within a range of 500-5000 rpm or 750-4000 rpm. As the speed increases, the average size of the droplets decreases.

Congealed particles are formed from the droplets. The congealed particles comprise the active agent, the gelling agent, the inorganic salt (if present in the aqueous suspension), the water-soluble polymer, and water. In some embodiments, the congealed particles further comprise a colorant. In any or all of the above embodiments, forming congealed particles may comprise cooling the droplets of the aqueous suspension to a temperature below the gelation temperature of the aqueous suspension. In some embodiments, cooling the droplets comprises convective cooling. The droplets are atomized into an atmosphere having a temperature below the gelation temperature of the aqueous suspension. As the droplets travel through the atmosphere, convective cooling occurs and the droplets congeal. In some embodiments, the droplets are atomized into a collection chamber or containment bag. The atmosphere within the collection chamber or containment bag may be air or an inert gas (e.g., nitrogen, argon, helium, or the like). In any or all of the above embodiments, the droplets may be atomized into an atmosphere having a temperature at least 5° C. below the gelation temperature of the aqueous suspension, such as a temperature at least 10° C., at least 15° C., or at least 20° C. below the gelation temperature. When using a collection chamber or containment bag, the atmosphere temperature may be selected such that the droplets congeal before striking a wall of the collection chamber or containment bag. In certain embodiments, the droplets are atomized into an atmosphere at ambient temperature (e.g., 15-25° C.).

FIG. 1 is a schematic diagram illustrating droplet formation by rotary atomization of an aqueous suspension and subsequent formation of congealed particles via convective cooling. An aqueous suspension 100 is dispensed onto a spinning disk 110. As the disk 110 spins, droplets 120 are formed and move toward a wall 130 of a cooling chamber or containment bag. The droplets 120 are cooled via convective cooling and congeal prior to striking the wall 130.

The congealed particles are dried to remove free water and form a plurality of dried particles. Drying may be performed by any suitable means including, but not limited to, tray drying and fluid bed drying. The drying temperature may be within a range of from ambient temperature to a temperature 5° C. below the gelation temperature of the aqueous suspension. In some embodiments, the drying temperature is within a range of 30-70° C., such as 40-70° C., 40-60° C., or 50-60° C. In some embodiments, the congealed particles are dried for a period of time sufficient to remove at least 98 wt %, at least 98.5 wt %, at least 99 wt %, at least 99.5 wt %, or all of the free water from the congealed particles, thereby providing a plurality of dried particles. Advantageously, the particles undergo little or no change in size when dried. In any or all of the above embodiments, the average particle diameter may decrease by 20%, 15%, or 10% as the congealed particles are dried to remove free water.

Figure 2:
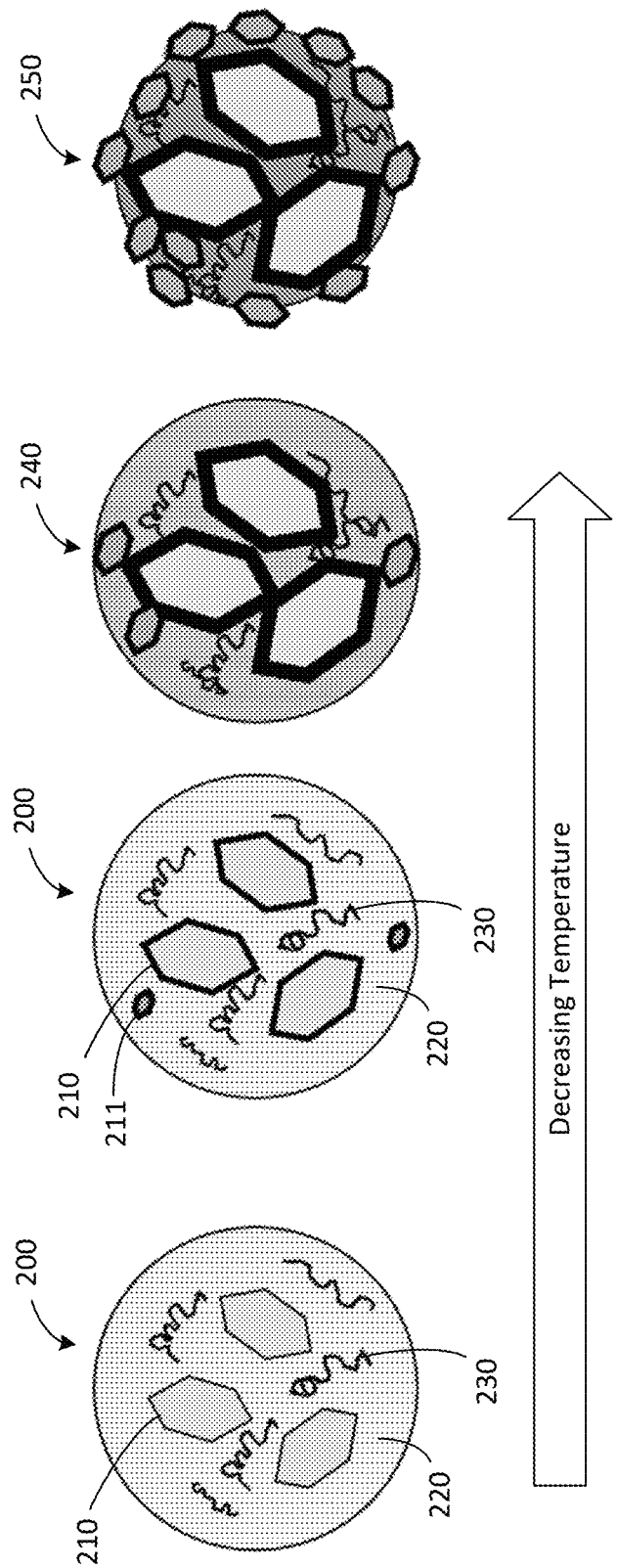
FIG. 2 is a schematic diagram illustrating solidification and congealing of an aqueous suspension by convective cooling.

Without wishing to be bound by a particular theory of operation, two solidification mechanisms may occur as the atomized droplets cool and congeal. Because the active agent is present in the aqueous suspension at a concentration above its solubility limit in the aqueous suspension, crystallization and/or crystal growth of the active agent occurs as the droplets cool. As the temperature drops, the gelling agent gels thereby forming congealed particles. Free water in the congealed particles is removed during the subsequent drying step. FIG. 2 is a schematic diagram illustrating solidification of an aqueous suspension comprising a crystalline active agent as disclosed herein. Droplets 200 of an aqueous suspension comprising crystals 210 of an active agent, dissolved gelling agent 220, and a water-soluble polymer 230 (the inorganic salt is not illustrated) are formed at a temperature above the gelation temperature of the aqueous suspension. As droplets 200 cool, growth of crystals 210 occurs along with formation of additional crystals 211 of active agent. As further cooling occurs, the gelling agent gels thereby forming congealed particles 240. The congealed particles are dried to remove free water, thereby forming dried particles 250.

In any or all of the above embodiments, forming the aqueous suspension may further comprise (i) combining a first portion of the active agent with water preheated to a temperature above the gelation temperature of the aqueous suspension and mixing to form an aqueous solution, (ii) adding the gelling agent and the water-soluble polymer to the aqueous solution and mixing to dissolve the gelling agent and the water-soluble polymer while maintaining the aqueous solution at a temperature above the gelation temperature, (iii) adding a second portion of the active agent to the aqueous solution to form the aqueous suspension, and (iv) maintaining a temperature of the aqueous suspension above the gelation temperature until forming the droplets of the aqueous suspension. Forming the aqueous suspension may further comprise adding the inorganic salt to the aqueous solution and mixing the aqueous solution while maintaining the aqueous solution at a temperature above the gelation temperature, wherein the inorganic salt is added after addition of the gelling agent and the water-soluble polymer and prior to addition of the second portion of the active agent. In certain embodiments, the first portion of the active agent (e.g., 10-60 wt % of a total amount of the active agent) is combined with a majority (e.g., 80-90%) of a total amount of water in the aqueous suspension, wherein the water is preheated to a temperature above the gelation temperature of the aqueous suspension. The first portion of the active agent is mixed in the water until all or substantially all of the first portion of the active agent is dissolved. In some embodiments, adding the active agent in two portions decreases variability in active agent crystal size in the resulting particles; when adding the active agent in a single addition, smaller crystals or particles may preferentially dissolve. In some embodiments, adding the gelling agent and the water-soluble polymer to the aqueous solution further comprises blending the gelling agent and the water-soluble polymer to form a blend, and then adding the blend to the aqueous solution. In any or all of the foregoing embodiments, adding the inorganic salt to the aqueous solution may further comprise dissolving the inorganic salt in water (e.g., 10-20% of the total amount of water in the aqueous solution) to form an inorganic salt solution, and then adding the inorganic salt solution to the aqueous solution. The inorganic salt solution may not be heated prior to adding it to the aqueous solution if the volume of salt solution is not sufficient to lower the temperature of the aqueous solution below the gelation temperature of the final aqueous suspension. In any or all of the above embodiments, the aqueous suspension may further comprise a colorant. In some embodiments, the colorant is added with the second portion of the active agent. The colorant may be blended with the second portion of the active agent prior to addition to the aqueous solution.

In any or all of the above embodiments, the method may further include applying a coating, e.g., a pharmaceutically acceptable coating, to the plurality of particles. The coating may be applied by any method known to a person of ordinary skill in the art including, but not limited to, fluid bed coating, pan coating, air suspension coating, spray coating, compression coating, solvent evaporation, and interfacial complexation, among others.

In any or all of the above embodiments, (i) the active agent may comprise caffeine, (ii) the water-soluble polymer may comprise PVP, or (iii) both (i) and (ii). In any or all of the above embodiments, the gelling agent may comprise gellan gum and the inorganic salt may comprise calcium chloride, or the gelling agent may comprise carrageenan and the inorganic salt may comprise potassium chloride.

IV. EXAMPLES

Example 1

Preparation of Multiparticulate Compositions

Suspensions having the compositions in Tables 1 and 2 were prepared as follows. In a first step, 90% of the total water was heated to 80-90° C. Approximately half of the caffeine was added and dissolved with mixing. PVP and the gelling agent (gellan gum or carrageenan) were dry blended together. The dry blend was added to the heated solution of caffeine and water, and mixed until the dry blend was dissolved. In a separate vessel, the inorganic salt (calcium chloride or potassium chloride) was dissolved in the remaining 10% of the water to form a salt solution, which was then added to the aqueous solution of caffeine, PVP, and gelling agent. The remaining caffeine and dye were mixed into the aqueous solution to form an aqueous suspension in which some of the caffeine remained suspended. The aqueous suspension was maintained at a temperature of 80-90° C.

The heated aqueous suspension was dispensed onto a spinning disk of a rotary atomizer. The disk had a diameter of 4" (10 cm) and was spinning at 800 rpm. Droplets were atomized into a containment bag. The collection temperature was room temperature. Droplets were cooled by convection cooling as they were atomized and traveled through the air in the containment bag. The droplets were liquid as they were spun off the rotating disk and congealed prior to striking the wall of the containment bag. The congealed particles were collected and dried in on a tray in an oven at a temperature of 50-60° C. until all free water was removed. The compositions of the dried particles (assuming removal of all water) are provided in Tables 1 and 2.

TABLE 1

| Component | Amount in Suspension (wt %) | Amount in Final Product (wt %) |
| --- | --- | --- |
| Water | 52.27 | — |
| Caffeine | 39.76 | 83.28 |
| PVP-K30 | 6.53 | 13.68 |
| Gellan gum | 0.94 | 1.97 |
| Calcium Chloride | 0.07 | 0.15 |
| Colorant (Blue Lake #2) | 0.44 | 0.92 |

TABLE 2

| Component | Amount in Suspension (wt %) | Amount in Final Product (wt %) |
| --- | --- | --- |
| Water | 50.35 | — |
| Caffeine | 41.89 | 84.37 |
| PVP-K30 | 6.29 | 12.67 |
| Carrageenan | 1.05 | 2.11 |
| Potassium Chloride | 0.28 | 0.56 |
| Colorant (Blue Lake #2) | 0.14 | 0.28 |

The effect of the caffeine on the gelation temperature of the aqueous suspension was determined by obtaining viscosity curves of (i) an aqueous suspension comprising 52.62 wt % water, 39.89 wt % caffeine, 6.53 wt % PVP-K30, 0.89 wt % gellan gum, and 0.07 wt % calcium chloride, and (ii) a comparable aqueous suspension that did not include caffeine but had the same mass ratios of PVP/gellan gum/calcium chloride (87.54 wt % water, 12.4 wt % PVP-K30, 1.49 wt % gellan gum, and 0.11 wt % calcium chloride). Viscosity was measured as follows. The solution was prepared as described above, and an impeller (overhead stirrer #VOS-PB-S41, VWR, Radnor, PA) was constantly mixing the solution. A jacketed reaction vessel (1000-mL jacketed reaction vessel, #CG-1930-24, Chemglass, Vineland, NJ)) was heated to the desired solution temperature using a heated circulating bath (Polystat heated circulating bath

Figure 3:
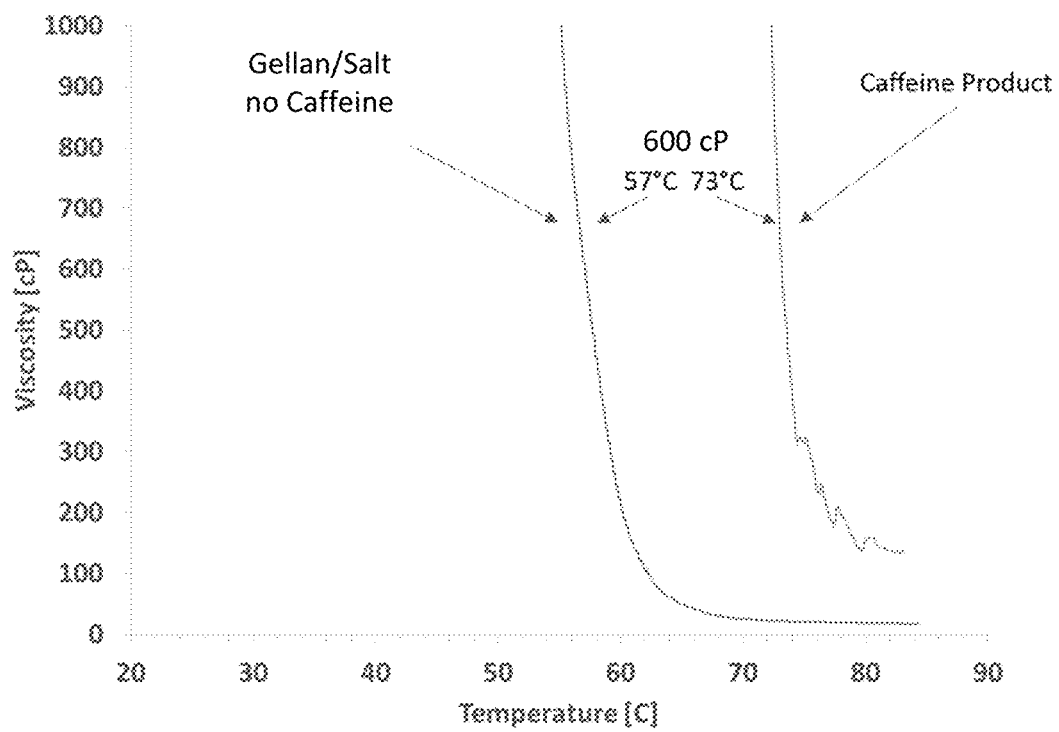
FIG. 3 is a graph of viscosity vs. temperature for aqueous suspensions with and without caffeine.

EW-12105-30, Cole Parmer, Vernon Hills, IL). With the impeller and viscometer (Hydramotion Reactavisc viscometer #RV3-150-TS, Hydramotion Ltd., Malton, U.K.) inserted into the vessel, the components were added as previously mentioned. Once the suspension had been added and a steady state achieved, the cooling process began. To cool the solution, the circulating bath heat was turned off and the fluid replaced with colder room temperature fluid. As the solution cooled, the viscosity and temperature data were recorded using a laptop and the ViscoLink 4 software (Hydramotion). Gelation was considered to have occurred when the viscosity exponentially increased, implying the solution had set up. As shown in FIG. 3, addition of caffeine to the aqueous suspension increased the temperature at which the viscosity was 600 cP from 57° C. to 73° C. The temperature of the aqueous suspension including caffeine was selected to be above the gelation temperature.

Figure 4:
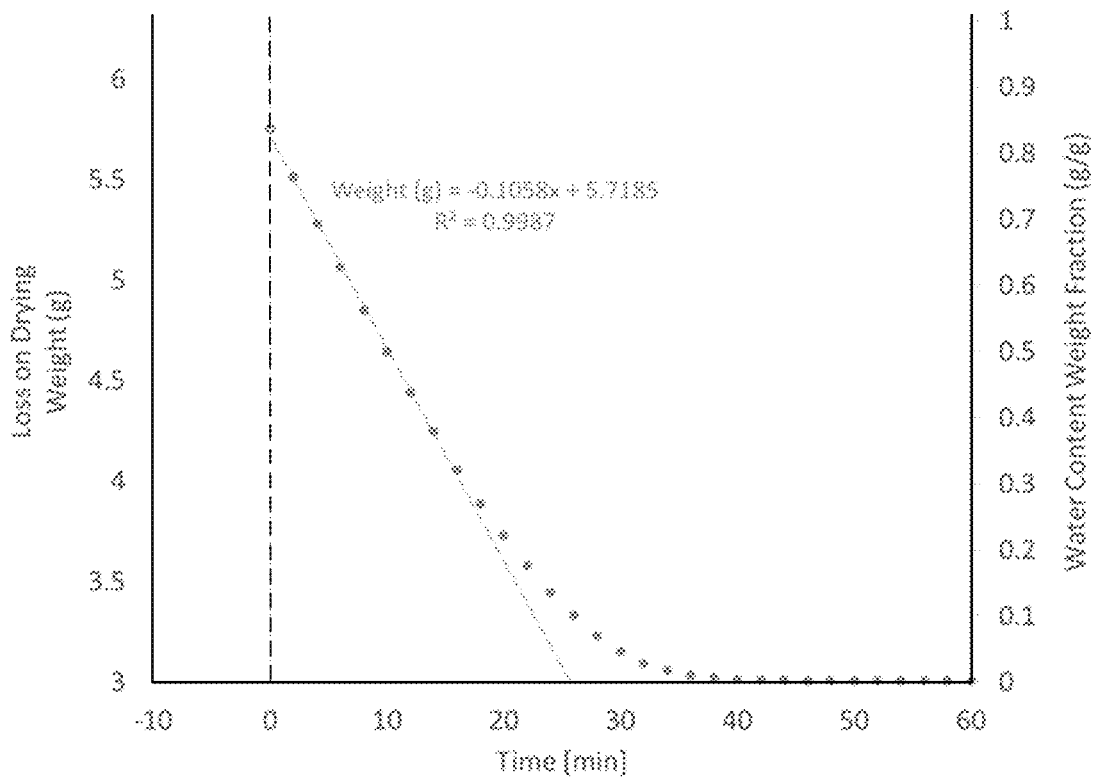
FIG. 4 is a graph showing water loss from a gelling multiparticulate composition comprising caffeine as disclosed herein during manufacture and upon further drying at 50-60° C.

Loss-on-drying (LOD) measurements showed that 16% of available water was lost from the multiparticulate compositions during the droplet formation and congealing process. The remaining water was rapidly lost while drying at 50-60° C. with essentially all water lost within 35 minutes (FIG. 4).

Example 2

Particle Characterization

Average particle diameters of the caffeine-loaded gelling multiparticulate composition formed by the process of Example 1 were determined by pressure titration at pressures o 0.1 bar, 1 bar, 2 bar, 3 bar, and 4 bar. Particle dispersion was performed using a Scirocco 2000 sample dispersion unit (Malvern Instruments Ltd, United Kingdom). Particle sizes were measured with a Malvern Mastersizer 2000 particle size analyzer (Model APA2000, Malvern Instruments Ltd, United Kingdom). Standard methods for light diffraction measurement of particle size include USP General Chapter 429, ISO 13320-1, and European Pharmacopoeia 2.9.31. The method described in USP General Chapter 429 was used for the present analysis. Mie theory was used to calculate particle size based on light diffraction. Briefly, a container of the caffeine-loaded gelling multiparticulate composition was mixed by inversion at least 10 times. An aliquot of the composition was added to the sample tray of the sample dispersion unit and distributed evenly. The sample feed rate was adjusted so that the obscuration was within the range of 1% to 6% for the majority of the analysis.

Figure 5:
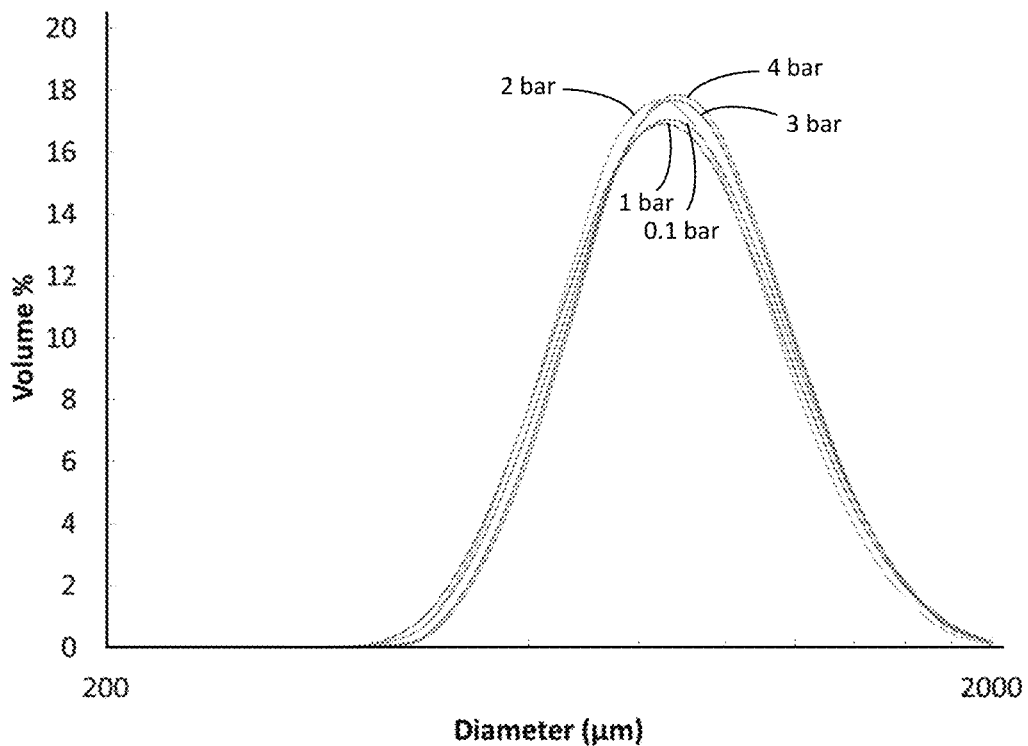
FIG. 5 is a graph of volume % vs. diameter, showing particle distribution sizes of a gelling multiparticulate composition comprising caffeine as disclosed herein when measured by pressure titration at pressures ranging from 0.1-4 bar.

The results are shown in FIG. 5 and Table 3. There was little or no significant change in the average particle size, indicating that the particles are robust.

TABLE 3

| Pressure (bar) | D(v0.1) μm | D(v0.5) μm | D(v0.9) μm | D[3.2] μm | D[4.3] μm | Span |
|---|---|---|---|---|---|---|
| 0.1 | 587 | 828 | 1197 | 803 | 866 | 0.738 |
| 1 | 575 | 816 | 1181 | 790 | 853 | 0.742 |
| 2 | 580 | 809 | 1153 | 787 | 844 | 0.709 |
| 3 | 602 | 838 | 1196 | 815 | 874 | 0.709 |
| 4 | 608 | 843 | 1198 | 820 | 879 | 0.700 |

Figure 6:
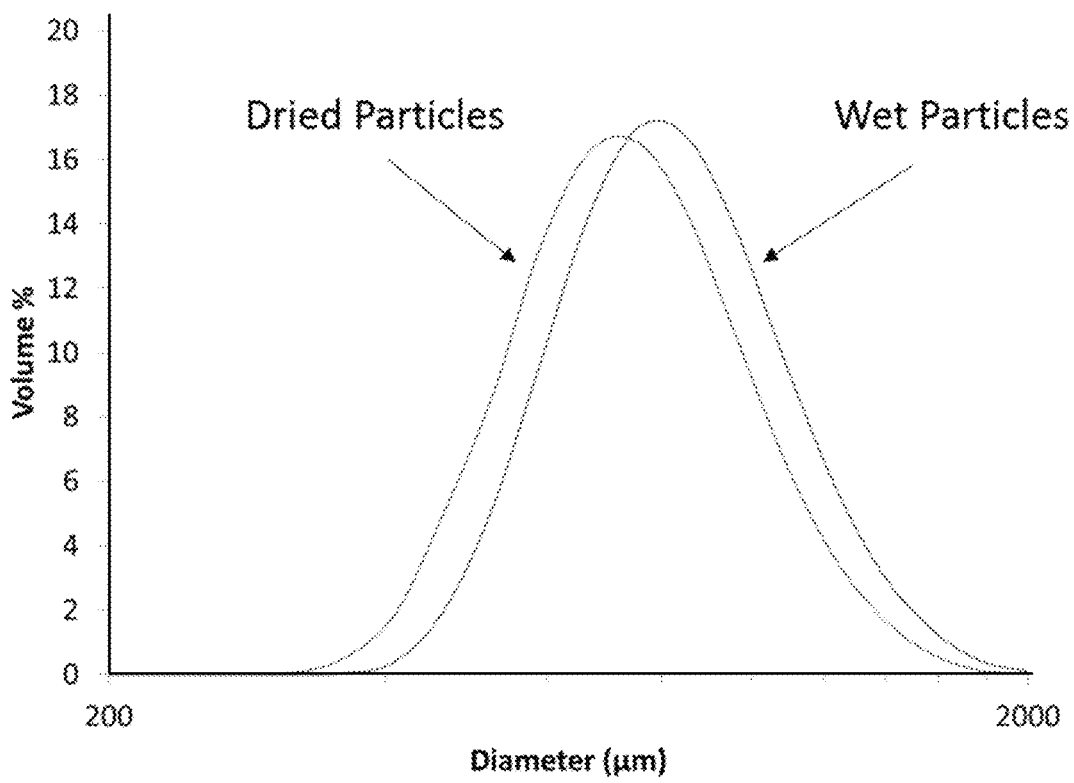
FIG. 6 is a graph comparing particle distribution sizes of congealed (wet) particles and dried particles a gelling multiparticulate composition comprising caffeine as disclosed herein.

Particle size analysis showed that the gelled particulates shrank by approximately 10% as they dried (FIG. 6).

Figure 7:
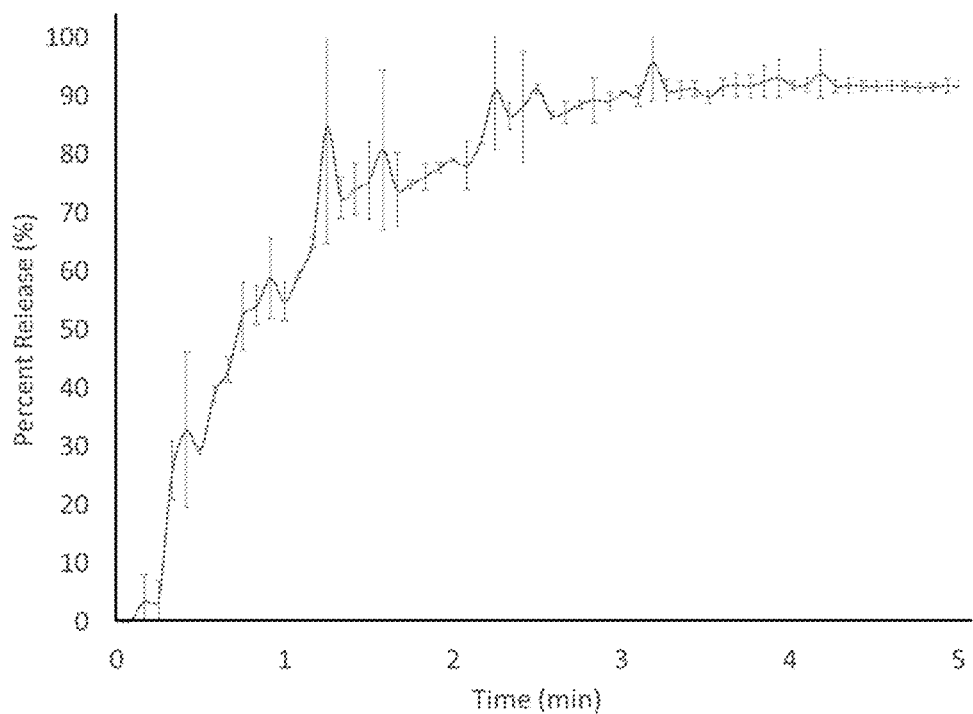
FIG. 7 is a graph illustrating rapid dissolution of a gelling multiparticulate composition comprising caffeine as disclosed herein.

Dissolution of the particles in aqueous media was evaluated as follows. Dissolution media was prepared by diluting concentrated HCl to 0.01 N, yielding a pH 2.0 solution. Standards were prepared by dissolving 5 mg caffeine in 100 mL of dissolution media. One-point standard calibration was used for dissolution analysis. The samples had a target of 5 mg caffeine. 100 mL of the dissolution media was added to a 100-mL vessel in a 37° C. water bath. USP apparatus 1 baskets were used for dosing. The sample was added to the basket and lowered into the dissolution media at time 0. The baskets were set to rotate at 255 rpm over the duration of the test. A spectrum was taken every 5 seconds using a Pion UV-VIS spectrometer (Pion, Inc., Billerica, MA). Analysis was done at a wavelength of 272 nm, with a zero baseline taken at 500 nm. As shown in FIG. 7, the particles dissolved rapidly with nearly 100% dissolution in less than 5 minutes.

Figure 8:
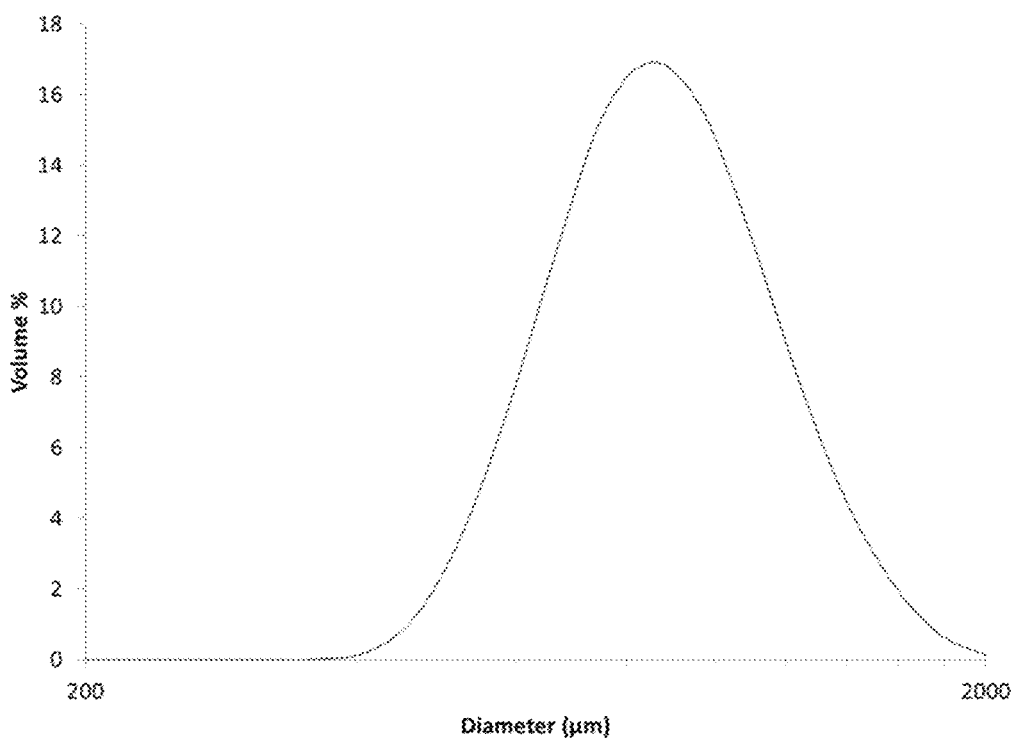
FIG. 8 is a graph illustrating average particle diameter of a gelling multiparticulate composition comprising caffeine as disclosed herein.

Laser diffraction analysis with a dispersive pressure of 0.1 bar showed that the caffeine-loaded multiparticulate composition formed by the process of Example 1 provided particles having an average volume mean diameter, D[4,3], of approximately 870 μm (FIG. 8).

The particle strength of the composition was evaluated by pressure titration at pressures ranging from 0.1-4 bar. Robustness was determined by calculating the change in $D_{10}$:

$$\Delta D_{10} = \frac{D_{10}^{4bar} - D_{10}^{0.1bar}}{D_{10}^{0.1bar}}$$

Figure 9:
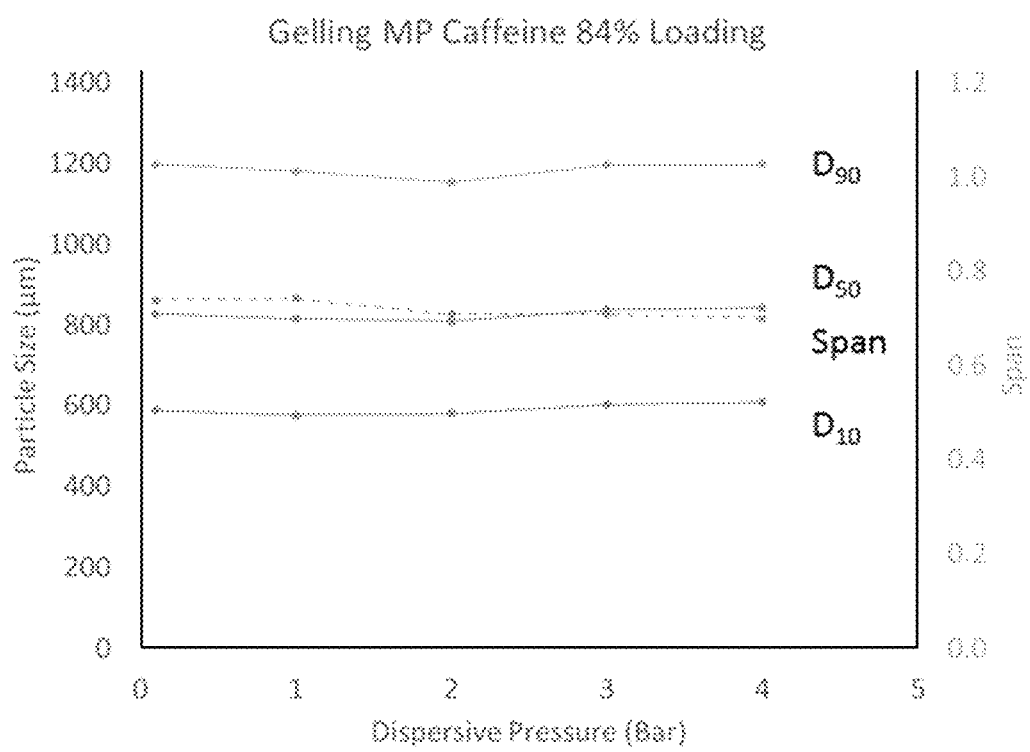
FIG. 9 is a graph showing particle size and span as a function of dispersive pressure for a gelling multiparticulate composition comprising 84 wt % caffeine as disclosed herein.

The results are shown in FIG. 9. The caffeine-loaded gelling multiparticulate composition formed by the process of Example 1 (Gelling MP) exhibited excellent results with a $\Delta D_{10}$ value of 4%, which may attributed to noise and indicates no attrition as the dispersive pressure increased from 0.1 bar to 4 bar.

Example 3

Gelled Phenytoin Multiparticulate Composition

A gelled phenytoin multiparticulate composition was prepared using the general procedure described in Example 1, wherein phenytoin was used in place of the caffeine. The composition is shown in Table 4.

TABLE 4

| Component | Suspension (wt %) | Final Product (wt %) |
|---|---|---|
| Water | 73.98 | — |
| Phenytoin | 20 | 76.87 |
| PVP-K30 | 4.62 | 17.77 |
| Gellan | 1.29 | 4.98 |
| Calcium Chloride | 0.1 | 0.38 |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A multiparticulate composition, comprising:
a plurality of gelled particles, comprising
>60 wt % of an active agent,
1 wt % to 6 wt % of a gelling agent comprising gellan gum, carrageenan, agar, pectin, gelatin, or any combination thereof,
0.05 wt % to 1 wt % of an inorganic salt, and
4 wt % to 34 wt % of a water-soluble polymer.

2. The multiparticulate composition of claim 1, wherein the gelling agent comprises gellan gum, carrageenan, or a combination thereof.

3. The multiparticulate composition of claim 1, wherein the inorganic salt comprises an alkali metal salt, an alkaline earth metal salt, or a combination thereof.

4. The multiparticulate composition of claim 1, wherein the inorganic salt is a chloride salt.

5. The multiparticulate composition of claim 1, wherein:
(i) the gelling agent comprises gellan gum and the inorganic salt comprises calcium chloride; or
(ii) the gelling agent comprises carrageenan and the inorganic salt comprises potassium chloride.

6. The multiparticulate composition of claim 1, wherein:
(i) a mass ratio of gelling agent to inorganic salt is within a range of 1 to 60;
(ii) a mass ratio of water-soluble polymer to gelling agent is within a range of 1 to 39;
(iii) a mass ratio of water-soluble polymer to inorganic salt is within a range of 4 to 800; or
(iv) any combination of (i), (ii), and (iii).

7. The multiparticulate composition of claim 1, wherein the plurality of gelled particles comprises from greater than 60 wt % to 95 wt % active agent.

8. The multiparticulate composition of claim 1, wherein the water-soluble polymer has a weight average molecular weight of 20,000 daltons to 200,000 daltons.

9. The multiparticulate composition of claim 1, wherein the water-soluble polymer comprises polyvinylpyrrolidone (PVP), a copolymer of vinylpyrrolidone and vinyl acetate (PVP-VA), polyethylene glycol (PEG), polyethylene oxide (PEO), or any combination thereof.

10. The multiparticulate composition of claim 1, wherein the plurality of gelled particles has an average diameter of from 100 μm to 2 mm as measured by laser diffraction.

11. The multiparticulate composition of claim 1, further comprising a colorant.

12. The multiparticulate composition of claim 1, further comprising an outer coating on gelled particles of the plurality of gelled particles.

13. A dosage form, comprising the multiparticulate composition of claim 1, wherein the dosage form is a capsule, a tablet, or a powder mix.

14. A method of making the multiparticulate composition of claim 1, the method comprising:
preparing an aqueous suspension comprising an active agent, a gelling agent, an inorganic salt, and a water-soluble polymer, wherein (i) the gelling agent comprises gellan gum, carrageenan, agar, pectin, gelatin, or any combination thereof, (ii) a concentration of the active agent in the aqueous suspension exceeds a solubility limit of the active agent in the aqueous suspension such that the active agent is not completely dissolved in the aqueous suspension, and (iii) a combined mass of the active agent, the gelling agent, and the water-soluble polymer includes >60 wt % of the active agent, 1 wt % to 6 wt % of the gelling agent, 0.05 wt % to 1 wt % of the inorganic salt, and 4 wt % to 34 wt % of the water-soluble polymer;
forming droplets of the aqueous suspension, wherein the droplets are formed at a temperature above a gelation temperature of the aqueous suspension;
cooling the droplets of the aqueous suspension below a gelation temperature of the aqueous suspension, whereby the gelling agent gels to form gelled particles comprising the active agent, the gelling agent, the water-soluble polymer, and water; and
drying the gelled particles.

15. The method of claim 14, wherein forming droplets of the aqueous suspension comprises dispensing the aqueous suspension onto a spinning disk of a rotary atomizer, whereby the aqueous suspension is atomized into droplets.

16. The method of claim 14, wherein cooling the droplets of the aqueous suspension comprises convective cooling.

17. The method of claim 14, wherein preparing the aqueous suspension further comprises:
combining a first portion of the active agent with water preheated to a temperature above the gelation temperature of the aqueous suspension and mixing to form an aqueous solution;
adding the gelling agent and the water-soluble polymer to the aqueous solution and mixing to dissolve the gelling agent and the water-soluble polymer while maintaining the aqueous solution at a temperature above the gelation temperature;
adding the inorganic salt to the aqueous solution and mixing the aqueous solution while maintaining the aqueous solution at a temperature above the gelation temperature;
adding a second portion of the active agent to the aqueous solution to form the aqueous suspension; and
maintaining a temperature of the aqueous suspension above the gelation temperature until forming the droplets of the aqueous suspension.

18. A multiparticulate composition, comprising:
a plurality of gelled particles, comprising
>60 wt % of an active agent,
1 wt % to 6 wt % of a gelling agent comprising gellan gum, carrageenan, agar, pectin, gelatin, or any combination thereof,
0.05 wt % to 1 wt % of an inorganic salt, and
0.1 wt % to 38.9 wt % of a water-soluble polymer,
wherein
(i) a mass ratio of gelling agent to inorganic salt is within a range of 1 to 60,
(ii) a mass ratio of water-soluble polymer to gelling agent is within a range of 1 to 39, and
(iii) a mass ratio of water-soluble polymer to inorganic salt is within a range of 4 to 800.

* * * * *